(12) United States Patent
Yamaguchi et al.

(10) Patent No.: US 7,042,557 B2
(45) Date of Patent: May 9, 2006

(54) SAMPLE SUPPLYING DEVICE FOR A DRY PARTICLE-SIZE DISTRIBUTION MEASURING APPARATUS AND METHOD

(75) Inventors: Tetsuji Yamaguchi, Kyoto (JP); Hiroyuki Kitamura, Kyoto (JP)

(73) Assignee: Horiba, Ltd., Kyoto (JP)

( * ) Notice: Subject to any disclaimer, the term of this patent is extended or adjusted under 35 U.S.C. 154(b) by 225 days.

(21) Appl. No.: 10/322,819

(22) Filed: Dec. 18, 2002

(65) Prior Publication Data

US 2003/0147074 A1    Aug. 7, 2003

(30) Foreign Application Priority Data

Dec. 19, 2001  (JP) .................. P. 2001-386360

(51) Int. Cl.
*G01N 1/00*    (2006.01)

(52) U.S. Cl. .................. 356/36; 356/336; 221/180

(58) Field of Classification Search ............... 198/758, 198/533; 209/241; 221/179, 180
See application file for complete search history.

(56) References Cited

U.S. PATENT DOCUMENTS

| | | | | |
|---|---|---|---|---|
| 2,956,487 A | * | 10/1960 | Giaimo, Jr. ............... 356/256 |
| 3,677,390 A | * | 7/1972 | Parker et al. ............. 221/173 |
| 3,730,386 A | * | 5/1973 | Monsees .................. 198/444 |
| 4,063,642 A | * | 12/1977 | Sticht et al. ............. 209/540 |
| 4,218,929 A | * | 8/1980 | Spurlin ..................... 74/61 |
| 4,552,262 A | * | 11/1985 | Murakami et al. ......... 198/447 |
| 4,869,811 A | * | 9/1989 | Wolanski et al. .......... 209/212 |
| 4,991,598 A | * | 2/1991 | Henderson et al. ........ 131/290 |
| 5,931,308 A | * | 8/1999 | Gesing et al. ............. 209/212 |

FOREIGN PATENT DOCUMENTS

| | | |
|---|---|---|
| JP | 04-248894 | 4/1992 |
| JP | 5-22073 | 3/1993 |
| JP | 06-027013 | 2/1994 |
| JP | 10-197437 | 7/1998 |
| JP | 11-207261 | 8/1999 |
| JP | 2001-1658457 | 6/2001 |
| JP | 2001-347189 | 12/2001 |

* cited by examiner

*Primary Examiner*—Gregory J. Toatley, Jr.
*Assistant Examiner*—Juan D. Valentin, II

(57) ABSTRACT

A dry particle-size distribution measuring apparatus and method is provided for suspending a plurality of bristle members across a support surface of a dispensing trough with bristles being arranged to contact and disperse any clusters of particles to a primary state prior to releasing the particles to a sample flow cell. A source of light can irradiate the sample flow cell and a detector unit can measure any scattered and/or diffracted light to provide corresponding signals. A control unit can determine the size and distribution of particles from the corresponding signals. The bristle members can be mounted on a brush unit that is directly mounted on the trough and both the trough and the brush unit can be driven by the same vibrator unit.

19 Claims, 4 Drawing Sheets

SAMPLE SUPPLYING DEVICE FOR A DRY PARTICLE-SIZE DISTRIBUTION MEASURING APPARATUS AND METHOD

BACKGROUND OF THE INVENTION

1. Field of the Invention

The present invention relates to a sample supplying device for a dry particle-size distribution measuring apparatus, and more particularly, to an improved sample supplying device and method of providing a preliminary dispersion of particles into a primary state during the initial introduction of the sample into the measuring apparatus.

2. Description of Related Art

In a dry particle-size distribution measuring apparatus, usually, a powdery and particulate sample is accommodated in a trough of a sample supplying device which is disposed above a measurement flow cell, and, when the particle-size distribution of the sample is to be measured, the trough may be vibrated by a linear feeder to drop the sample through a drop hole formed in the trough, thereby causing the sample to be supplied into a conduit connected to the flow cell.

However, relatively small particles in a sample, such as powdery and particulate members are sometimes aggregated by an electrostatic force, a Van der Waals force, a magnetic force, or the like which acts among the powdery and particulate members even in a dry state, so that the powdery and particulate members are not formed as so-called primary particles in which powdery and particulate members are completely separated from each other, but rather may be formed as secondary particles (in each of which several primary particles are aggregated) or tertiary particles (in each of which several secondary particles are aggregated). When such powdery and particulate members including not only primary particles but also secondary and tertiary particles are supplied to a flow cell as a sample and measurement is then conducted while irradiating the sample with light, it is difficult to obtain a true particle-size distribution of the powdery and particulate members.

In conventional sample supplying devices, therefore, there has been attempts to employ the following techniques: (1) a sieve member is disposed under the drop hole with a size to prevent such secondary and tertiary particles from being dropped and thereby allow only powdery and particulate members of a predetermined size or smaller relative to the sieve size to be passed; and (2) a plurality of bearing balls are placed in the sieve member, and secondary and tertiary particles are dispersed by rotation and sliding contact with the bearing balls to change them into primary particles.

In both of the above techniques, however, it is difficult to attain a complete state in which a powdery and particulate sample is configured only by primary particles and does not contain secondary and tertiary particles, and additionally the sieve can sometimes be clogged by secondary and tertiary particles, so that powdery and particulate members cannot be smoothly dropped in a predetermined quantity. Particularly, in the case where a sample of a high density is supplied by vibration of a linear feeder, and so-called submicron powdery and particulate members in which the particle size is smaller than 1 µm are charged as a sample, there arises a disadvantage that only dispersion up to 1 µm which corresponds to the secondary particle state may be performed.

Thus, there remains a need in this field of particle measurement to provide a compact and economical solution to these problems.

SUMMARY OF THE INVENTION

It is an object of the invention to provide a sample supplying device in which, even when a powdery and particulate sample contains secondary and tertiary particles, these particles can be preliminarily dispersed to be changed into a primary particle state before the particles are dropped by vibration of a trough, thereby enabling the powdery and particulate sample to be stably supplied in the desired primary particle state and in a predetermined and controlled drop quantity.

In order to attain this objective, in a sample supplying device for a dry particle-size distribution measuring apparatus which is configured by a trough that accommodates a sample, and uses a linear feeder that vibrates the trough, and in which the sample in the trough is dropped from a sample drop hole formed in the trough, by vibrating the trough, a brush which is positioned within the trough to be vertically vibrated due to vibration of the trough and the sample is dispersed by vibration of the brush.

In the sample supplying device, a brush unit is disposed in the trough which forward feeds powdery and particulate members by vibration in upward and forward directions to drop the members therefrom, and the brush unit is vertically vibrated by the vibration of the trough. When a powdery and particulate sample accommodated in the trough contains secondary and tertiary particles, the secondary particles and the like are dispersed (pulverized) by the brush bristles which are vertically vibrated, to be changed to primary particles, and then dropped from the sample drop hole while maintaining the primary particle state. Consequently, the powdery and particulate members are dropped and supplied into a flow cell in the desired primary particle state.

A method of separating particles into a primary state for a particle-size distribution measuring apparatus includes supplying a sample of particles to a support surface, vibrating the support surface to move the particles to a dispensing portion, and contacting the sample with a plurality of bristles that vibrates to the support surface prior to the dispensing portion, the arrangement of bristles being spaced to assure contact with any cluster of particles to dispense them into a primary particle state.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide a sample supplying device and method for a dry particle-size distribution measuring apparatus of measuring particles in a primary state.

Figure 1:
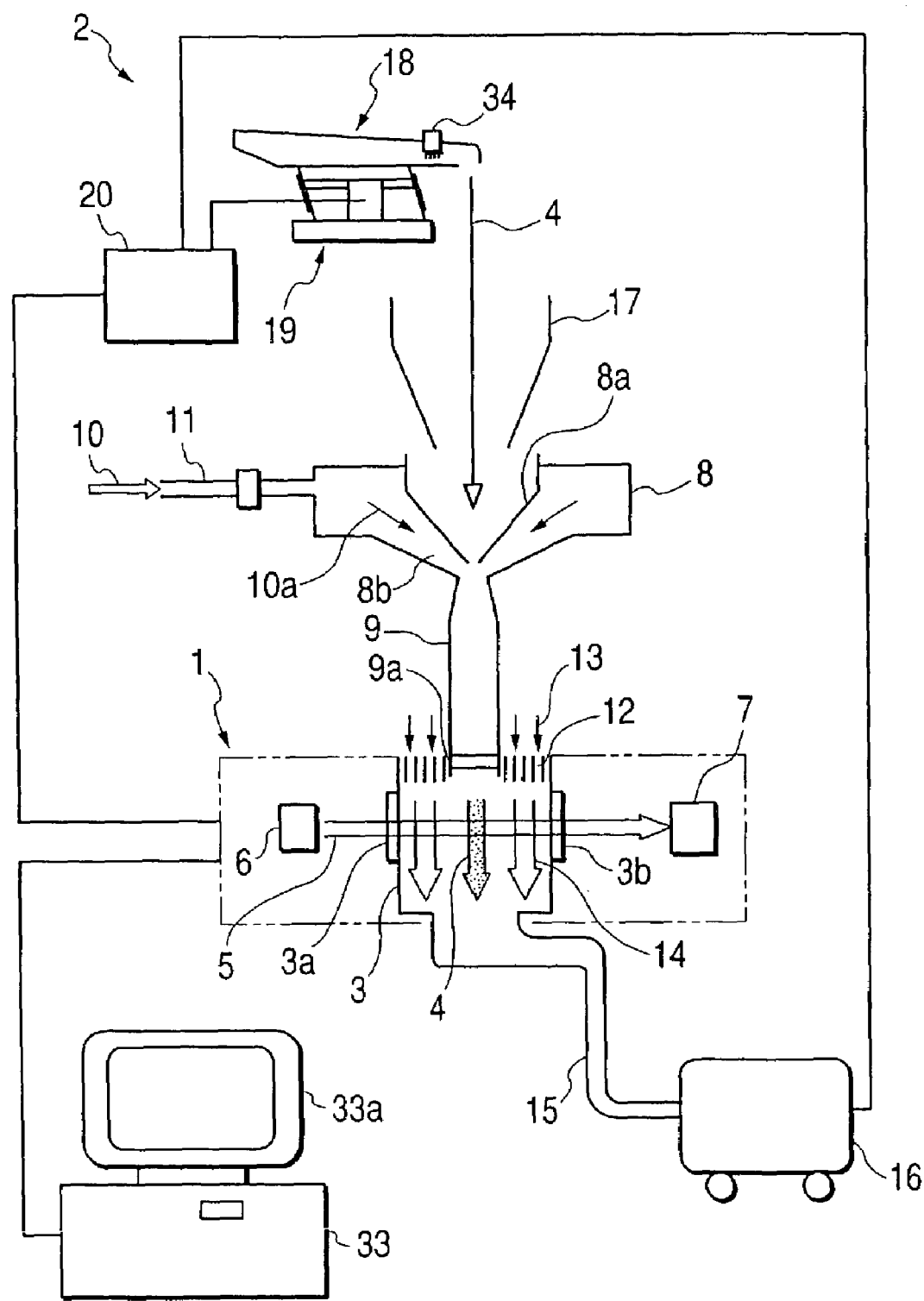
FIG. 1 is a view schematically showing a schematic diagram of a dry particle-size distribution measuring apparatus into which the sample device of the invention is incorporated.
Figure 2:
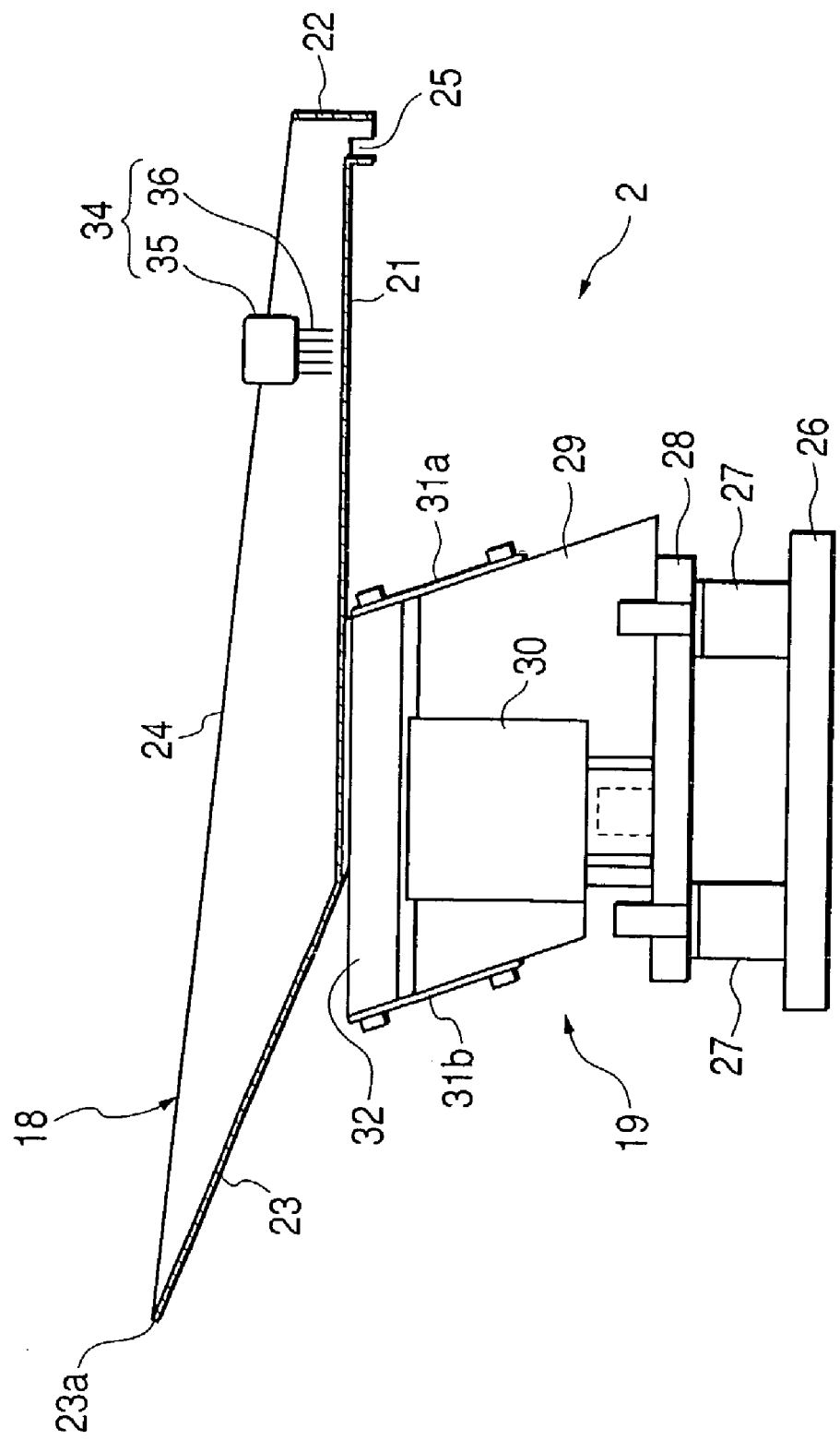
FIG. 2 is a schematic side cross sectional view showing an example of a sample supplying device of the invention.

Hereinafter, the invention will be described in detail with references to the Figures. FIGS. 1 to 3 show one embodiment of the invention. FIG. 1 schematically shows a configuration of a dry particle-size distribution measuring apparatus into which the sample supplying device of the invention is incorporated. In the Figure, 1 denotes a measuring section, and 2 denotes a sample supplying device disposed above the measuring section 1.

The measuring section 1 is configured for example in the following manner. The reference numeral 3 denotes a tubular flow cell or measurement cell which is vertically disposed to receive the sample. Optical windows 3a and 3b are formed in opposed side faces of the flow cell 3, respectively. A laser light source 6 can irradiate a sample 4 that is dropped in the flow cell 3 with a laser beam 5. Laser source 6 is placed outside one of the optical windows such as optical window 3a. An optical detecting section 7 which receives scattered light and/or diffracted light that is produced by irradiating the sample 4 with the laser beam 5 is placed outside the other optical window 3b. Measurement of the light contacting the particles by the detecting section 7 permits a determination of particle size.

The reference numeral 8 denotes an ejector device which serves as a sample introducing section disposed immediately above the flow cell 3, and which includes a funnel-shaped section 8a. A sample guiding section 9 which communicates with the flow cell 3 is positioned under the funnel-shaped section 8a. A gas supply path 11 for compressed air 10 is connected to the ejector device 8. An air flow path 8b which guides the compressed air 10 supplied through the compressed air supply path 11, into the sample guiding section 9 is formed on the side of the lower face of the funnel-shaped section 8a, so that compressed air 10a flowing in the air flow path 8b is blown as a dispersion flow to the sample 4 being dropped from a trough 18 (described later) of the sample supplying device 2. The lower end of the sample guiding section 9 is insertedly connected to the flow cell 3. In a lower end portion of the guiding section, there is a partitioning section 9a which extends to the vicinities of the upper ends of the optical windows 3a and 3b. The reference numeral 12 denotes straightening guide vanes which are disposed around the portion of the sample guiding section 9 and are insertedly connected to the flow cell 3, so as to be in parallel with the partitioning section 9a, and through which outside air 13 is sucked or aspirated into the flow cell so that a sheath flow 14 is formed in the flow cell 3 by the sucked outside air 13 about the sample.

The reference numeral 15 denotes a sample recovery flow path which is formed on the lower end side of the flow cell 3, and which comprises a suction or vacuum apparatus 16. The reference numeral 17 denotes a hopper which is disposed above the ejector 8, and which is used for guiding the sample 4 that is dropped from the trough 18 of the sample supplying device 2, into the ejector device 8.

The configuration of the sample supplying device 2 will be described with reference also to FIGS. 2, 3A, and 3B. The sample supplying device 2 is configured mainly by the trough 18 which accommodates the powdery and particulate sample 4, and a linear feeder 19 which can vibrate the trough 18. The vibration of the linear feeder 19 is controlled by a controller 20.

The configuration of the trough 18 will be described with reference to FIGS. 2 and 3A. The trough 18 is configured with a bottom support surface portion 21 which has a thin isosceles trapezoidal shape in a plan view; a front plate portion 22 which extends upward from the short edge side (hereinafter, referred to as the front end side) of the bottom portion so as to be perpendicular to the bottom portion 21; a rear plate portion 23 which has an isosceles trapezoidal shape, and which extends from an end on the long edge side (hereinafter, referred to as the rear end side) of the bottom portion in an upward inclined direction with respect to the rear end portion of the bottom portion 21; and side plate portions 24 which extend upward from lateral sides of the bottom portion 21 so as to couple the front plate portion 22 with the rear plate portion 23. The trough is formed into a box-like shape which has a thin isosceles trapezoidal shape in a plane view, and in which the upper side is opened for receiving samples. As shown in FIG. 3A, the trough 18 has a tapered shape in a plan view, and is configured so that, as seen from FIG. 2, the height of the front plate portion 22 is lower than the level of the rear top 23a of the rear plate portion 23 so that a larger quantity of the sample 4 can be placed and accommodated on the rear end side. The reference numeral 25 denotes a sample drop hole or a dispensing portion which is opened in the bottom portion 21 and in close proximity to the front plate portion 22, and which is formed into a rectangular shape in a plan view so as to extend over the whole lateral length of the bottom portion 21. The trough 18 is preferably made of a material which has an adequate mechanical strength and a property of not adsorbing the sample 4, and which is nonmagnetizable in consideration of the linear feeder 19 that will be described later. Examples of such a material are stainless steel and an appropriate synthetic resin.

The configuration of the linear feeder 19 will be described with reference to FIG. 2. The reference numeral 26 denotes a pedestal on which a base 28 is horizontally held via vibration proof pieces 27 made of rubber or the like. The reference numeral 29 denotes an electromagnet fixing unit which is disposed on the upper face of the base 28, and to which an electromagnet 30 is fixed. The reference numerals 31a and 31b denote a pair of plate springs which are separated from each other by an adequate distance. The lower ends of the plate springs are fixed to the side faces of the electromagnet fixing unit 29 in such a manner that the plate springs are parallel to each other and inclined in a rearward direction (in a leftward direction in FIG. 2). An attractive driving piece 32 having a plate-like shape in which the upper and lower faces are parallel to each other is held in a horizontal state on the upper ends of the plate springs. The attractive driving piece 32 is made of a material which is attracted by a magnetic attractive force, such as iron. The attractive driving piece 32 is disposed in a state where its upper face is fixed to the bottom portion 21 of the trough 18 and a small gap is formed between the lower face and an attractive face of an upper portion of the core of the electromagnet 30. The pair of plate springs 31a and 31b are used for converting the vertical vibration into longitudinal vibration, and are configured so that the pressing force of one (the rear end side) of the plate springs or the plate spring 31b is stronger than that of the other (the front end side) plate spring 31a. In a normal state where the electromagnet 30 is not energized, the bottom portion 21 assumes a resting horizontal posture.

In the sample supplying device 2, when a rectangular pulse voltage in which the lowest level is 0 V and the highest level is several volts is applied to the coil of the electromagnet 30, the attractive driving piece 32 is intermittently attracted to the electromagnet at a constant period, whereby vibration is applied to the trough 18 in the upward and forward directions while using the masses of the electromagnet 30 and the base 28 as a reaction force. This vibration causes the sample 4 which is placed and accommodated in the trough 18, to be moved toward the front end side of the trough 18, so that the sample can be dropped from the sample drop hole 25.

As can be appreciated, vibration can be provided by other devices such as shaker units and other mechanical units and the electromagnetic drive force is only a preferred embodiment.

Referring again to FIG. 1, 33 denotes a control unit with a calculation and control section which is configured by, for example, a personal computer, and which controls the whole apparatus. Furthermore, the calculation and control section has functions of calculating the particle-size distribution of the sample 4 on the basis of an output signal from the measuring section 1 and by using an arithmetic expression according to Fraunhofer analytic theory or Mie scattering theory, displaying a result of the calculation on a displaying device 33a, and storing the calculation result into a memory section which is disposed in the apparatus, or a memory card or a memory disc which can be detachably attached to the apparatus.

As described above, in this configured sample supplying device 2, vibration caused by the linear feeder 19 is applied to the trough 18, and the sample 4 placed on the trough 18 is moved forward in the trough 18 by the force vector of vibration along the horizontal axis of the trough 18, so that the sample can be dropped from the sample drop hole 25 which is opened in the front end side of the trough 18. In the sample supplying device 2 of this embodiment, a brush unit 34 which is vertically vibrated due to the vibration of the trough 18 is disposed in the trough 18 and on the upstream side of the drop hole 25 in the direction of moving the sample, so that the sample 4 is dispersed by contact with the vibration of the brush unit 34 before the sample is dropped.

Figure 3A:
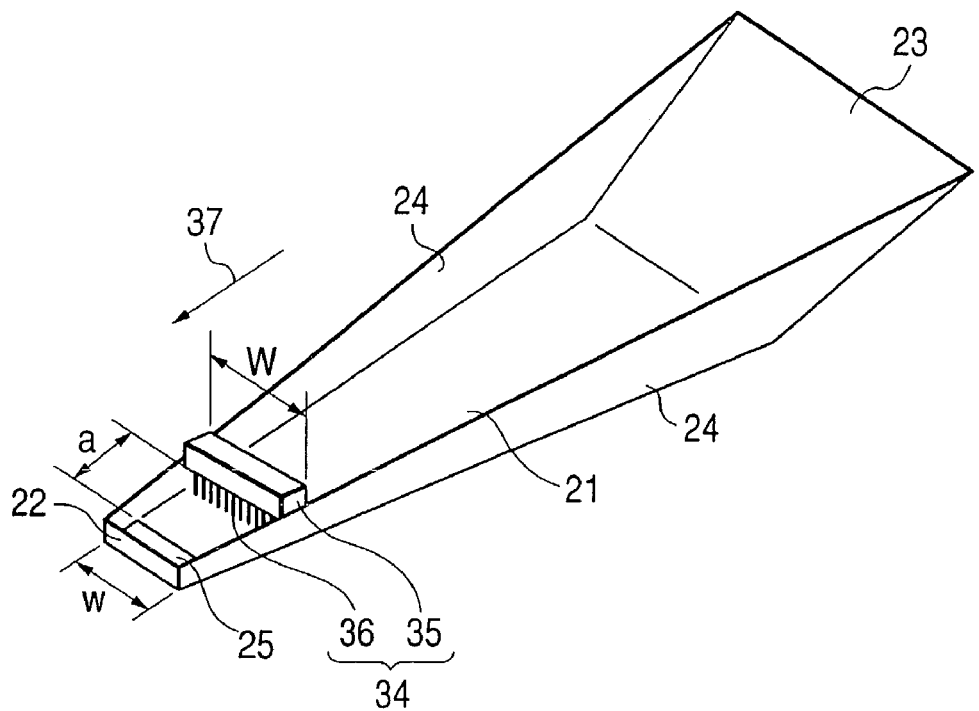
FIG. 3A is a perspective view showing an example of a trough and a brush unit.
Figure 3B:
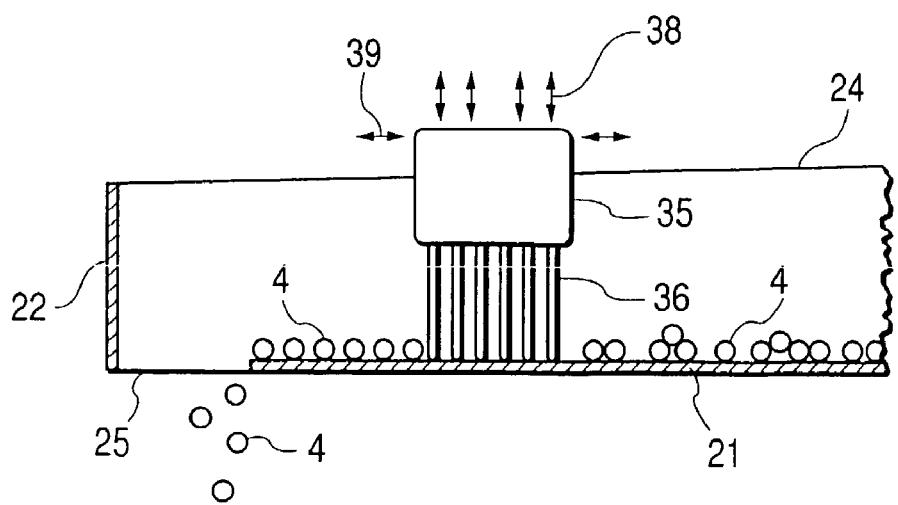
FIG. 3B is a partial enlarged cross sectional view illustrating the arrangement of the brush unit in the trough.
Figure 4A:
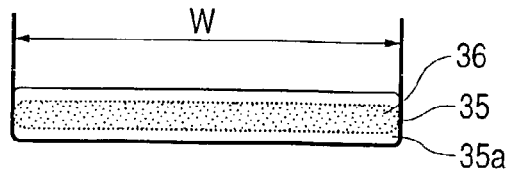
FIG. 4A is a schematic of a first arrangement of brush bristles.

The brush unit 34 is configured by a holder 35 and bristles 36 implanted into the holder, and as shown in FIG. 3A is laterally placed in the trough 18 so that the longitudinal direction of the brush is perpendicular to the advancing direction 37 of the sample 4. The holder 35 can have, for example, an elongated rectangular parallelepiped shape, and as shown in FIG. 4A the plurality of the bristles 36 are evenly implanted in the bottom face 35a of the brush 34 and spaced to insure operative contact with any cluster of particles. More specifically, the width W in the longitudinal direction of the holder 35 is slightly larger than the width w of the front plate portion 22, and the width of the trough 18 in a plan view is gradually more reduced in a direction moving toward the front plate portion 22. Therefore, the holder 35 is blocked by the lateral side plate portions 24 of the trough 18 at a position which is in the upstream side in the direction of moving the sample 4 and separated from the sample drop hole 25 by an adequate distance a. At the blocked position, the holder is vibrated in vertical directions indicated by the bidirectional arrow 38 in FIG. 3B, and slightly moved in forward and rearward directions indicated by the bidirectional arrow 39. The holder 35 can be made of an adequate supporting material such as a synthetic resin, and the bristles 36 can be made of a synthetic resin such as nylon or metal wires.

When appropriate powdery and particulate members are placed as the sample 4 in the rear end side of the trough 18 and a predetermined pulse voltage is applied to the electromagnet, the trough 18 is vibrated, and the vibration of the trough 18 causes the sample 4 to forward move in the direction indicated by the arrow 37 in FIG. 3A. In this case, the brush unit 34, for example, of a rectangular parallelepiped shape is laterally disposed in the trough 18, and the bristles 36 are vertically and horizontally vibrated due to the vibration of the trough 18, at the position which is separated and upstream from the sample drop hole 25 by the distance a.

The powdery and particulate sample 4 which is advanced from the rear end side of the trough 18 to the front end side is initially blocked by the bristles 36 of the brush 34 and then enters below the bristles 36 which are vertically vibrated. In this case, primary particles contained in the powdery and particulate sample 4 will generally pass between the bristles 36 because the primary particles are smaller in size than the gaps between the bristles 36, but clusters of secondary and tertiary particles cannot pass between the bristles 36 because the secondary and tertiary particles are larger in size than the gaps. The secondary and tertiary particles are pulverized and dispersed by the bristles 36 which are vertically vibrated, to be changed to primary particles. The powdery and particulate sample 4 which has passed through the brush 34 is advanced toward the sample drop hole 25 by the vibration of the trough 18, and then dropped from the sample drop hole 25 to be supplied into the flow cell 3 via the hopper 17, the ejector 8, and the sample guiding section 9.

As described above, the brush unit 34 is disposed so as to be perpendicular to the direction 37 of feeding the sample 4 and to move relative to the sample in the vibrating trough 18 which is used for forward feed of the sample 4 by vibration in the upward and forward directions, and the brush unit 34 is vertically vibrated by the vibration of the trough 18. If the sample 4 accommodated in the trough 18 contains secondary and tertiary particles, the secondary particles and the like are dispersed (pulverized) by the brush unit 34 which is vertically vibrated, to be changed to primary particles, and then dropped from the sample drop hole 25 while maintaining the primary particle state. Therefore, the sample 4 is dropped and supplied into the flow cell 3 in the desired primary particle state for measurement purposes.

In this case, the driving force of vertically vibrating the brush unit 34 for pulverizing secondary particles and the like is realized only by the vibration of the trough 18, and the brush unit 34 is vertically vibrated in the tapered trough 18 while being separated by the constant distance a from the sample drop hole 25. Therefore, a special driving apparatus for the brush unit 34, parts for fixing the vibration position, and the like are not required as long as the brush is secured in position but permits relative movement to the trough 18.

When the intensity of the vibration of the trough 18 is adequately adjusted, the quantity of the powdery and particulate sample 4 to be dropped can be controlled with excellent quantitativeness. For example, the vibration frequency and intensity are changed about 65±10 Hz, duty ratio 20% (it can be changed 0 to 100% in response to particular sizes of samples) of which a pulse intensity is about 0–5 V (rectangular waves).

Figure 4B:
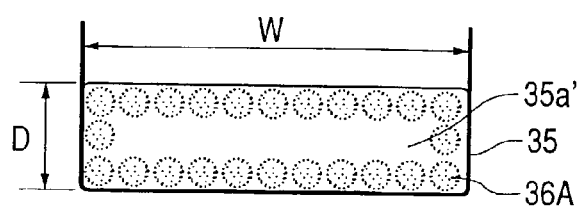
FIG. 4B is a schematic of a second arrangement of brush bristles.

The shape of the brush unit 34 is not restricted to that of the above embodiment, and may be variously modified. For example, the manner of implanting the bristles 36 may be modified in the following manner. As shown in FIG. 4B, small groups 36A each configured by several to several tens of bristles 36 may be formed, and the small groups 36A may be continuously formed in the periphery of the bottom face (hereinafter, referred to as the implanted face) 35a of the holder 35 in which the depth D is slightly larger. The bristles 36 may not be disposed in a center area 35a of the implanted face 35a.

Figure 4C:
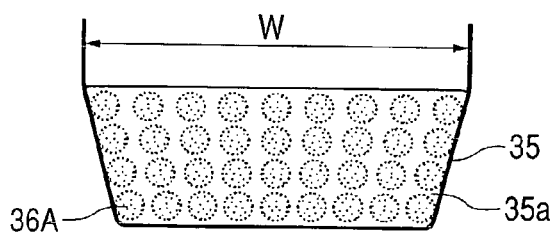
FIG. 4C is a schematic of a third arrangement of brush bristles.

The holder 35 in FIGS. 4A and 4B has a rectangular parallelepiped shape, and the implanted face 35a is rectangular (the face may be square). Alternatively, as shown in FIG. 4C, the implanted face 35a may be trapezoidal. In the alternative, when the length of the long edge is not shorter than W, the implanted face is not always required to have an isosceles trapezoidal shape.

Figure 4D:
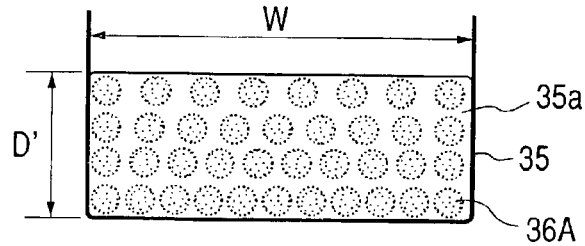
FIG. 4D is a schematic of a fourth arrangement of brush bristles.

As shown in FIG. 4D, the depth D of the implanted face 35a may be set to be large, and the small groups 36A may be disposed in a large number over the whole area of the implanted face 35a.

Figure 4E:
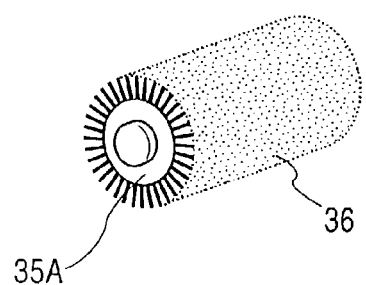
FIG. 4E is a schematic of a fifth arrangement of brush bristles.

As shown in FIG. 4E, a cylindrical member (or a columnar member) 35A having a length W may be used as the holder 35, and the bristles 36 may be densely implanted to the peripheral face of the member. The cylindrical member 35A can be mounted to rotate while being vibrated.

The trough 18 should have a tapered shape in a plan view in which the portion on the side of the sample drop hole 25 is narrowed, but it is not always required to have an isosceles trapezoidal shape. The sample drop hole 25 which is formed in the front end side of the bottom portion 21 of the trough 18 is not required to have a rectangular shape in a plan view, and may have any shape such as a square, a circle, or an oval.

In the preferred embodiment, the trough 18 is held in such a manner that the bottom portion 21 is horizontal when stationary. Alternatively, the bottom portion 21 may be inclinedly disposed so that the portion on the side of the sample drop hole 25 is provided at a lowered position.

Thus, a sample supplying device for a dry particle-size distribution measuring apparatus is configured by a trough that accommodates a sample, and a linear feeder that vibrates the trough. The sample in the trough is dropped from a sample drop hole formed in the trough, by vibrating the trough. A brush which is vertically vibrated due to vibration of the trough is disposed in the trough, and the sample is dispersed by vibration of the brush. Even a small size powdery and particulate sample accommodated in the trough containing secondary and tertiary particles are dispersed (pulverized) by bristles which are vertically vibrated, to be changed to primary particles, and then dropped from the sample drop hole while maintaining the primary particle state. Consequently, the powdery and particulate sample can be supplied in a desired primary particle state and in a predetermined and controlled drop quantity.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. In a sample supplying device for a dry particle-size distribution measuring apparatus which is configured by a trough that accommodates a sample, and a linear feeder that vibrates said trough, and in which the sample in said trough is dropped through a sample drop hole formed in said trough, by vibrating said trough, the improvement of an impacting member for separating any plurality of primary particles aggregated together comprising:
   a brush unit positioned in said trough and operatively mounted to vibrate in a plane transverse to a surface of the trough by the vibration of the trough to contact and pulverize any aggregated groups of the sample to a primary particle state before being dropped by gravity through the sample drop hole.

2. The sample supply device of claim 1, wherein the sample contains particles of approximately 1 μm in size and the brush unit includes bristles that are spaced greater than 1 μm in distance apart.

3. The sample supply device of claim 2, wherein the brush unit includes a cylindrical base with bristles extending 360° around the base.

4. The sample supply device of claim 1, further including a mounting unit for mounting the brush unit to provide both vertical and horizontal movement in said trough.

5. The sample supply device of claim 1, wherein the brush unit includes bristles that are progressively positioned closer to each other the closer to the sample drop hole.

6. The sample supply device of claim 1, wherein the brush unit includes bristles that are positioned in an elongated arrangement across said trough.

7. The sample supply device of claim 1, wherein the brush unit includes bristles arranged in rectangular pattern with center devoid of bristles.

8. A method of separating particles into a primary state of single particles in a particle-size distribution measuring apparatus, comprising the steps of:
   supplying a sample of particles to a support surface;
   vibrating the support surface to move the sample of particles along the support surface to a dispense position; and
   contacting the sample of particles upstream of the dispense position with a plurality of bristles that vibrate relative to the support surface, the arrangement of bristles being spaced to assure impact contact with any cluster of particles attached together whereby the bristles will contact and disperse the cluster of particles to a primary state after impact with the bristles so that the sample of particles will be in a primary state after contact with the bristles.

9. The method of claim 8, wherein the sample of particles are approximately 1 μm in size and the bristles are spaced from each other at a distance approximately slightly greater than 1 μm.

10. The method of claim 8, wherein the bristles are vibrated in a vertical and horizontal direction relative to the support surface.

11. The method of claim 10, wherein the bristles are operatively mounted above the support surface and are vibrated by the vibration of the support surface to contact and pulverize the cluster of particles.

12. A device for separating particles into a primary state of single particles in a particle-size distribution measuring apparatus, comprising:
   a support member for receiving sample particles;
   means for supplying a sample of particles to a surface of the support member;

a vibrating unit operatively connected to the support member for moving the sample of particles by a vibratory movement to a release position on the support member; and a plurality of bristles that vibrate relative to the support surface between the means for supply and the release position whereby the bristles will contact and disperse by breaking any clusters of sample particles into a primary state so that the sample of particles will be in a primary state after contact with the bristles.

13. The device of claim 12 wherein the support member is a trough with a substantially horizontal support surface that only moves by the vibratory movement.

14. The device of claim 13 wherein the support surface is tapered in a direction towards the release position.

15. The device of claim 14 wherein the support member is made of a synthetic resin.

16. The device of claim 12 wherein the vibrating unit includes a spring unit and an electromagnetic drive unit to provide a longitudinal vibration to the support member.

17. The device of claim 16 wherein the plurality of bristles are mounted on a holder that is attached to the support member to enable vertical and horizontal movement of the plurality of bristles relative to the support surface by the operation of the vibrating unit.

18. The device of claim 17 wherein individual bristles are spaced on the holder at a distance slightly greater than a diameter of the primary state of particle size.

19. The device of claim 18 wherein the bristles are formed of a synthetic resin.

* * * * *